(12) United States Patent
Kono et al.

(10) Patent No.: US 7,179,783 B2
(45) Date of Patent: Feb. 20, 2007

(54) SULFURIC ACID AMINE SALT, SULFONIC ACID AMINE SALT, PRODUCTION THEREOF AND SOFTENER COMPOSITION

(75) Inventors: Jun Kono, Wakayama (JP); Tomokatsu Kusumi, Wakayama (JP); Akira Sakaguchi, Wakayama (JP); Yasuki Ohtawa, Wakayama (JP); Ikuo Sugano, Wakayama (JP); Kazutaka Shiratsuchi, Wakayama (JP); Shuji Tagata, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/332,161

(22) Filed: Jan. 17, 2006

(65) Prior Publication Data

US 2006/0116314 A1   Jun. 1, 2006

Related U.S. Application Data

(63) Continuation of application No. 10/417,122, filed on Apr. 17, 2003, now abandoned.

(30) Foreign Application Priority Data

Apr. 17, 2002  (JP)  .............. 2002-114282
Jul. 26, 2002  (JP)  .............. 2002-217686

(51) Int. Cl.
    *C11D 1/65*  (2006.01)
(52) U.S. Cl. ..................................... 510/493
(58) Field of Classification Search ............ None
    See application file for complete search history.

(56) References Cited

U.S. PATENT DOCUMENTS

| | | | |
|---|---|---|---|
| 4,447,343 A | 5/1984 | May et al. |
| 4,476,045 A | 10/1984 | O'Lenick |
| 4,548,810 A | 10/1985 | Zofchak |
| 4,661,270 A | 4/1987 | Grandmaire et al. |
| 4,751,009 A | 6/1988 | Damaso et al. |
| 5,409,621 A | 4/1995 | Ellis et al. |
| 6,218,354 B1 | 4/2001 | Demeyere et al. |
| 6,486,120 B1 | 11/2002 | Porta et al. |
| 6,528,070 B1 | 3/2003 | Bratescu et al. |
| 6,617,303 B1 | 9/2003 | Smith et al. |

FOREIGN PATENT DOCUMENTS

| | | |
|---|---|---|
| DE | 146467 | 2/1981 |
| EP | 0 609 574 A1 | 8/1994 |
| JP | 5-106166 A | 4/1993 |
| JP | 10-298867 A | 11/1998 |
| JP | 2001-200474 A | 7/2001 |
| JP | 2001-526304 A | 12/2001 |
| WO | WO-96/12000 A1 | 4/1996 |
| WO | WO-97/00929 A1 | 1/1997 |
| WO | WO-98/20964 A2 | 5/1998 |

OTHER PUBLICATIONS

Keyes et al., J. Oral Ther. Pharmacol., vol. 3, No. 3, pp. 157-173 (1966) (Abstract only).

*Primary Examiner*—John R. Hardee
(74) *Attorney, Agent, or Firm*—Birch, Stewart, Kolasch & Birch, LLP

(57) ABSTRACT

Provided is a process for preparing a sulfuric acid amine salt (I) represented by the formula (I), which is a neutralization compound between a sulfated compound having a long chain alkyl or alkenyl group and an amine having a long chain alkyl or alkenyl group, useful as softener.

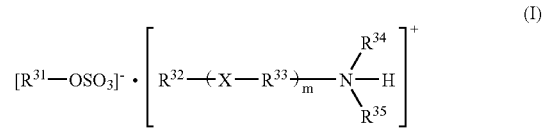

wherein $R^{31}$ is a linear or branched $C_{18-36}$ alkyl or alkenyl group, or a group represented by the formula $R^{36}$—$(OA)_n$- (wherein $R^{36}$ is a linear or branched $C_{12-36}$ alkyl or alkenyl group, OA is an oxyalkylene group having 2 to 4 carbon atoms and n is a number of from 0.1 to 10 on average), $R^{32}$ is a is a linear or branched $C_{10-36}$ alkyl or alkenyl group, X is —CONH—, —NHCO—, —COO— or —OCO—, $R^{33}$ is a linear or branched $C_{1-6}$ alkylene group, $R^{34}$ is a linear or branched $C_{1-6}$ alkyl or hydroxyalkyl group, or a group represented by $R^5$—$[B-R^6]_b$—, $R^{35}$ is a linear or branched $C_{1-6}$ alkyl or hydroxyalkyl group, wherein $R^5$ is a linear or branched $C_{10-36}$ alkyl or alkenyl group, $R^6$ is a linear or branched $C_{1-6}$ alkylene group, B is a group selected from the group consisting of —COO—, —OCO—, —CONH— and —NHCO—, b is a number of 0 or 1 and m is a number of 0 or 1. A sulfonic acid amine salt may be obtained.

7 Claims, No Drawings

SULFURIC ACID AMINE SALT, SULFONIC ACID AMINE SALT, PRODUCTION THEREOF AND SOFTENER COMPOSITION

CROSS-REFERENCE TO RELATED APPLICATIONS

The present application is a 37 C.F.R. § 1.53(b) continuation of U.S. application Ser. No. 10/417,122, filed Apr. 17, 2003, now abandoned which claims priority on Japanese Application Nos. 2002-114282 filed Apr. 17, 2002, and 2002-217686 filed Jul. 26, 2002. The entire contents of each of these applications is hereby incorporated by reference.

TECHNICAL FIELD OF THE INVENTION

The present invention relates to new compounds for a softener, a production process therefor and compositions containing the same. Furthermore, the present invention relates to a production process for softener compositions and softener compositions obtained by means of production process.

PRIOR ART

Triethanolamine salt and the like has been heretofore known, for example sulfuric acid amine salt like an alkyl or alkenyl sulfuric amine salts, and used in various kinds of detergents and softeners. However, no sufficient study has been so far conducted on a neutralization compound between a sulfated compound having a long chain alkyl or alkenyl group and an amine having a long chain alkyl or alkenyl group.

Liquid softeners having been traditionally used in individual households contain a water non-soluble quaternary ammonium salt as a softening agent. Moreover, a study has been conducted on combination of an anionic surfactant therewith for the purpose of improving hand touch feeling and a softening effect. Disclosed in U.S. Pat. No. 4,447,343 is a technique using a combination of a quaternary ammonium compound with an anionic surfactant. Disclosed in U.S. Pat. No. 4,751,009 is a softener composition containing a cationic surfactant and a salt of a specific amine and an anionic surfactant. Disclosed in U.S. Pat. No. 4,661,270 is a transparent softener composition containing an anionic surfactant and a cationic surfactant. Besides, the present inventors propose a softener composition containing a monoalkyl cationic surfactant and an anionic surfactant for improvement on hand touch feeling in JP-A 2001-200474.

As to production processes for a softener, on the other hand, a method has been studied that suppresses an increase in viscosity and gelation in compounding. Disclosed in JP-A 10-298867 is a technique that an ammonium compound and sugar-alcohol are kneaded in advance, followed by mixing them with water under a high shearing. Disclosed in JP-W 2001-526304 is a production process for a softener in which a molten softening agent is dispersed in water. Disclosed in JP-A 5-106166 is a production process for a softener including a process in which a melt of a softening agent and a nonionic surfactant is produced. Furthermore, disclosed in U.S. Pat. No. 4,751,009 is a production process in which a sulfonic acid surfactant salt of a specific amine compound is mixed into a quaternary ammonium salt in advance. As described in U.S. Pat. No. 4,751,009, however, gelation frequently occurs in producing a softener composition containing an anionic surfactant and an amine compound. In order to avoid gelation, it is necessary to agitate softening agents under a high shearing energy. Moreover, even with such agitation adopted, a gel-like material locally remains, but is not easily dispersed even when the composition is added into water for rinsing clothes and then is agitated, resulting in another problem of reducing a softening effect. An improvement has been demanded.

DISCLOSURE OF THE INVENTION

It is an object of the present invention to provide a neutralization compound between a sulfuric acid or sulfonic acid having a long chain alkyl or alkenyl group and an amine having a long chain alkyl or alkenyl group, useful as a softener and a production process therefor.

It is another object of the present invention to provide a production process for a softener composition containing an amine compound and an anionic surfactant, under which gelation of the softener composition is suppressed, resulting in providing a sufficient softening effect.

The present invention is directed to a process for preparing a sulfuric acid amine salt (I) represented by the formula (I):

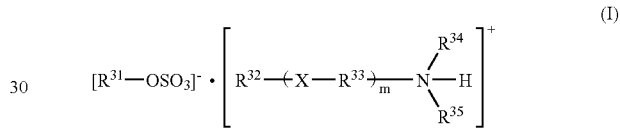

wherein in the formulae, $R^{31}$ is a linear or branched $C_{12-36}$ alkyl or alkenyl group, or a group represented by the formula $R^{36}$—$(OA)_n$-, wherein $R^{36}$ is a linear or branched $C_{12-36}$ alkyl or alkenyl group, OA is an oxyalkylene group having 2 to 4 carbon atoms and n is a number of from 0.1 to 10 on the average; $R^{32}$ is a linear or branched $C_{10-36}$ alkyl or alkenyl group; X is —CONH—, —NHCO—, —COO— or —OCO—; $R^{33}$ is a linear or branched $C_{1-6}$ alkylene group; $R^{34}$ is a linear or branched $C_{1-6}$ alkyl or hydroxyalkyl group, or a group represented by $R^5$—$[B—R^6]_b$—, wherein $R^5$ is a linear or branched $C_{10-36}$ alkyl or alkenyl group, $R^6$ is a linear or branched $C_{1-6}$ alkylene group, B is a group selected from the group consisting of —COO—, —OCO—, —CONH— and —NHCO—, b is a number of 0 or 1; $R^{35}$ is a linear or branched $C_{1-6}$ alkyl or hydroxyalkyl group; and m is a number of 0 or 1, comprising mixing and neutralizing a compound represented by the formula (III) (hereinafter referred to as the compound (III)):

wherein $R^{31}$ indicates the same meaning as in the above description, which has been obtained by sulfating an alcohol (hereinafter referred to as an alcohol (II)) represented by the formula (II):

wherein $R^{31}$ indicates the same meaning as in the above description, with a molten amine (hereinafter referred to as an amine (IV)) represented by the formula (IV):

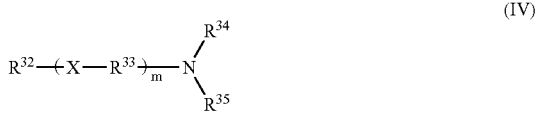

wherein in the formula, $R^{32}$, X, $R^{33}$, $R^{34}$, $R^{35}$ and m indicate the respective same meanings as in the above description.

The invention moreover provides a process for preparing a sulfonic acid amine salt (I') represented by the formula (I'):

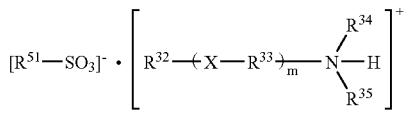

wherein $R^{51}$ is a linear or branched $C_{12\text{-}36}$ alkyl or alkenyl group or an $C_{12\text{-}36}$ alkylaryl group, $R^{32}$ is a linear or branched $C_{10\text{-}36}$ alkyl or alkenyl group; X is —CONH—, —NHCO—, —COO— or —OCO—; $R^{33}$ is a linear or branched $C_{1\text{-}6}$ alkylene group; $R^{34}$ is a linear or branched $C_{1\text{-}6}$ alkyl or hydroxyalkyl group, or a group represented by $R^5$—[B—$R^6$]$_b$—, wherein $R^5$ is a linear or branched $C_{10\text{-}36}$ alkyl or alkenyl group, $R^6$ is a linear or branched $C_{1\text{-}6}$ alkylene group, B is a group selected from the group consisting of —COO—, —OCO—, —CONH— and —NHCO—, b is a number of 0 or 1; $R^{35}$ is a linear or branched $C_{1\text{-}6}$ alkyl or hydroxyalkyl group; and m is a number of 0 or 1, comprising mixing and neutralizing a compound represented by the formula (III') (hereinafter referred to as the compound (III')):

$$R^{51}\text{—}SO_3H \quad (III')$$

wherein $R_{51}$ is defined above, which has been obtained by sulfonating a compound (II') represented by the formula (II'):

$$R^{51}\text{—}H \quad (II')$$

wherein $R^{51}$ indicates the same meaning as above, with a molten amine (hereinafter referred to as an amine (IV)) represented by the formula (IV):

wherein $R^{32}$, X, $R^{33}$, $R^{34}$, $R^{35}$ and m indicate the respective same meanings as in the above description.

It is preferable that the added amount of the compound (III) is equal to or less than an amine (IV) in mole and the compound (III) is added into the amine (IV) which is in advance mixed with a solvent.

The present invention is directed to a sulfuric acid amine salt (I) or a sulfonic acid amine salt (I'), obtained by the above shown production processes, respectively. Furthermore, the present invention is directed to use of the compound (I) or (I') obtained by the above production process as a softener.

Moreover, the present invention is directed to a sulfuric acid amine salt (hereinafter referred to as a sulfuric acid amine salt (I")) represented by the formula (I"):

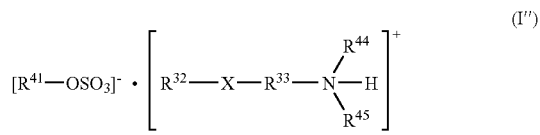

wherein in the formula, $R^{41}$ is a linear or branched $C_{18\text{-}36}$ alkyl or alkenyl group or a group represented by the formula $R^{36}\text{-}(OA)_n\text{-}$ (wherein $R^{36}$ is a linear or branched $C_{18\text{-}36}$ alkyl or alkenyl group, OA is an oxyalkylene group having 2 to 4 carbon atoms and n is a number of from 0.1 to 10 on average), $R^{32}$ is a linear or branched $C_{10\text{-}36}$ alkyl or alkenyl group, X is —CON—, —NHCO—, —COO— or —OCO—, $R^{33}$ is a linear or branched $C_{1\text{-}6}$ alkylene group, each of $R^{44}$ and $R^{45}$ is, independently of the other, a hydrogen atom, a linear or branched $C_{1\text{-}6}$ alkyl, alkenyl or hydroxyalkyl group or a group represented by the formula $R^{32}\text{—}X\text{—}R^{33}\text{—}$, (wherein $R^{32}$, X and $R^{33}$ indicate the respective above meanings).

The sulfuric acid amine salt (I") can be obtained by the process, as above shown, for producing (I).

The present invention also provides a composition containing a sulfuric acid amine salt (I), a sulfonic acid amine salt (I') or a sulfuric acid amine salt (I") described above and a solvent. Furthermore, the present invention also provides an application to a softener of a sulfuric acid amine salt (I), a sulfonic acid amine salt (I') or a sulfuric acid amine salt (I") described above.

The present invention provides a process for producing a softener composition including: a step (hereinafter referred to as Step A) of mixing in advance a compound (a) represented by the formula (1) and a compound (b) having one $C_{12\text{-}36}$ hydrocarbon group and one group selected from the group consisting of —$SO_3H$ and —$OSO_3H$ with each other in advance to obtain a surfactant mixture; and a step (hereinafter referred to as Step B) of dissolving and/or dispersing the thus obtained surfactant mixture in water:

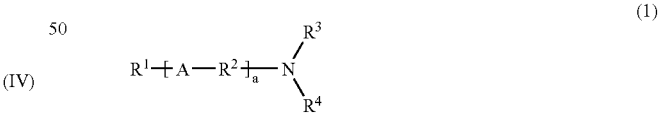

wherein in the formula, $R^1$ is a linear or branched $C_{10\text{-}36}$ alkyl or alkenyl group, $R^2$ is a linear or branched $C_{1\text{-}6}$ alkylene group, A is a group selected from the group consisting of —COO—, —OCO—, —CONH— and —NHCO—, a is a number of 0 or 1, $R^3$ is a linear or branched $C_{1\text{-}6}$ alkyl or hydroxyalkyl group or a group represented by $R^5$—[B—$R^6$]$_b$— and $R^4$ is a linear or branched $C_{1\text{-}6}$ alkyl or hydroxyalkyl group, wherein $R^5$ is a linear or branched $C_{10\text{-}36}$ alkyl or alkenyl group, $R^6$ is a linear or branched $C_{1\text{-}6}$ alkylene group, B is a group selected from the group consisting of —COO—, —OCO—, —CONH— and —NHCO— and b is a number of 0 or 1.

It is optional as to a production process for a softener composition described above that in Step A, an organic solvent is further mixed, together with water (d), as a component (c) or in Step A, water is further mixed as a component (d) so that a mass ratio of (d) component/[(a) component+(b) component] is in the range of 0.5/99.5 to 20/80.

The present invention, furthermore, provides a softener composition obtained by means of the production process described above.

DETAILED DISCLOSURE OF THE INVENTION

In sulfuric acid amine salts (I″) of the present invention, $R^{41}$ is a linear or branched $C_{18-36}$ alkyl or alkenyl group, or a group represented by the formula $R^{36}\text{-}(OA)_n\text{-}$, wherein $R_{36}$ is a linear or branched $C_{12-36}$ alkyl or alkenyl group, preferably exemplified by a stearyl group, an arachidyl group, a behenyl group, an oleyl group, a linol group, an alkyl group obtained by removing a hydroxy group from a $C_{12-36}$ Guerbet alcohol, a group obtained by adding ethylene oxide, propylene oxide or a mixture thereof to a group described above (an average number of moles added is 4 or less), more preferably a linear or branched $C_{18-24}$ alkyl group, the most preferably a branched alkyl group obtained by removing a hydroxy group from a $C_{18-24}$ Guerbet alcohol.

$R^{32}$ is a linear or branched $C_{10-36}$ alkyl or alkenyl group, preferably exemplified by a decyl group, a lauryl group, a myristyl group, a palmityl group, a stearyl group, an arachidyl group, a behenyl group, an oleyl group, a linol group or at least one kind selected from the group consisting of an alkyl or alkenyl group obtained by removing a carboxyl group from each of natural fatty acids such as beef tallow fatty acid, a hardened beef tallow fatty acid, palm oil fatty acid or a hardened palm oil fatty acid, particularly preferably a $C_{12-22}$ alkyl group.

$R^{33}$ is a linear or branched $C_{1-6}$ alkylene group and a $C_{1-3}$ alkylene group is preferable.

Each of $R^{44}$ and $R^{45}$ is, independently of the other, a hydrogen atom, a linear or branched $C_{1-6}$ alkyl, alkenyl or hydroxyalkyl group, or a group represented by the formula $R^{32}\text{—}X\text{—}R^{33}\text{—}$. An alkyl $C_{1-3}$ group is preferable.

X indicates —CONH—, —NHCO—, —COO— or —OCO— and preferable are —CONH—, —NHCO— and —COO—, and particularly preferable is —CONH—.

A sulfuric acid amine salt (I) of the present invention is obtained by mixing for neutralization a compound (hereinafter referred to as the compound (III)) represented by the formula of (III):

$$R^{31}\text{—OSO}_2\text{OH} \tag{III}$$

wherein $R^{31}$ indicates the same meaning as in the above description, which is obtained by sulfation of an alcohol (hereinafter referred to as an alcohol (II)) represented by the formula (II):

$$R^{31}\text{—OH} \tag{II}$$

wherein $R^{31}$ indicates the same meaning as in the above description, and a molten amine (hereinafter referred to as an amine (IV)) represented by the formula (IV):

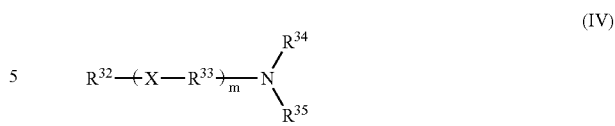

(IV)

wherein $R^{32}$, X, $R^{33}$, $R^{34}$ and $R^{35}$ are the same meanings as in the above description.

The sulfonic acid amine salt (I′) represented by the formula (I′) can be obtained by:

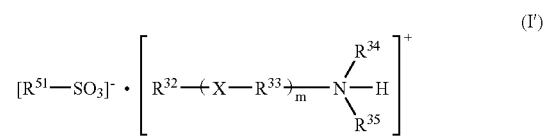

(I′)

wherein $R^{51}$ is a linear or branched $C_{12-36}$ alkyl or alkenyl group or an $C_{12-36}$ alkylaryl group, $R^{32}$ is a linear or branched $C_{10-36}$ alkyl or alkenyl group; X is —CONH—, —NHCO—, —COO— or —OCO—; $R^{33}$ is a linear or branched $C_{1-6}$ alkylene group; $R^{34}$ is a linear or branched $C_{1-6}$ alkyl or hydroxyalkyl group, or a group represented by $R^5\text{—}[B\text{—}R^6]_b\text{—}$, wherein $R^5$ is a linear or branched $C_{10-36}$ alkyl or alkenyl group, $R^6$ is a linear or branched $C_{1-6}$ alkylene group, B is a group selected from the group consisting of —COO—, —OCO—, —CONH— and —NHCO—, b is a number of 0 or 1; $R^{35}$ is a linear or branched $C_{1-6}$ alkyl or hydroxyalkyl group; and m is a number of 0 or 1, comprising mixing and neutralizing a compound represented by the formula (III′) (hereinafter referred to as the compound (III′)):

(III′)

wherein $R^{51}$ is defined above, which has been obtained by sulfonating a compound (II′) represented by the formula (II′):

(II′)

wherein $R^{51}$ indicates the same meaning as above, with a molten amine (hereinafter referred to as an amine (IV)) represented by the formula (IV):

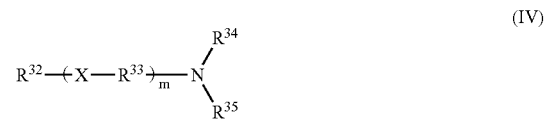

(IV)

wherein $R^{32}$, X, $R^{33}$, $R^{34}$, $R^{35}$ and m indicate the respective same meanings as in the above description.

It is preferable that m is 1 so that the obtained compound may have a lower melting point.

Note that since the compound (III) easily decomposes and cannot be preserved, it is required in the method of the present invention that the compound (III) obtained by sulfating an alcohol (II) is immediately neutralized with an amine (IV).

An example will be shown of a production process of the present invention below:

An alcohol (II) is sulfated in a common sulfation method using $SO_3$ gas diluted with dry air or inert gas in a thin film continuous sulfation facility, the gas and a sulfated compound are separated from each other by a cyclone and immediately thereafter, the sulfated compound and a molten amine (IV) are mixed for neutralization.

It was confirmed with various kinds of analyses (NMR, IR and the like) that no decomposition of sulfuric acid or sulfonic acid or the amine (IV) was observed to form a neutralization compound and that the amine (IV) in excess remained in its original state.

A reaction temperature in sulfation is preferably in the range of 20 to 80° C. A molar ratio of an alcohol (II) to $SO_3$ (alcohol(II)/$SO_3$) in reaction is preferably in the range of 0.80 to 1.20.

In the present invention, a mixed ratio (mol ratio) of the compound (III) to an amine (IV) ((III)/amine(IV))is preferably 1 or less and more preferably in the range of 0.1 to 1 from the viewpoint of preventing the decomposition of the compound (III).

Although a temperature of the compound (III) and an amine (IV) in neutralization is required to be in the range in which the amine (IV) is in a molten state, lower temperatures in the range are preferred and when the temperature in neutralization is excessively higher than the melting point of an amine (IV) by 30° C. or more, deterioration in quality arises in some case. Since the neutralization reaction is exothermic, cooling may be applied for control of a temperature.

In a production process of the present invention, a solvent is not always required when the compound (III) and an amine (IV) are mixed with each other, and when the molten amine (IV) and a solvent-free compound (III) are adopted in a thin film sulfation facility, a production process can be easily performed without using a solvent. However, an added amine (IV) is inevitably used in the form of liquid. It may be accordingly mixed at a temperature equal to or higher than the melting point of the amine (IV) or alternatively placed in a liquid state by use of a solvent. With addition of a solvent, not only can an amine (IV) be placed in a liquid state at low temperatures, but a viscosity of the system can also be reduced. Thereby, a neutralization temperature can be lowered to suppress degradation in quality in neutralization and to facilitate handling. It is not necessary to add the solvent to the system if the melting point and viscosity of the amine (IV) are sufficiently low or the solvent included in the compound (I) raises any problem in use.

As solvents used in the present invention, no specific limitation is placed on any particular kind and a solvent is preferably used as far as it is a liquid at 30° C. and capable of dissolving an amine (IV) thereinto. Solvents used in the present invention each preferably have a hydroxyl group, exemplified by one or more kinds selected from a monovalent or divalent alcohol with a $C_{1-10}$ hydrocarbon, or an alkylene oxide adduct thereto (wherein the hydrocarbon group may have either a branch chain or interrupted with an ether group in the main chain), wherein a value of log P of a solvent is preferably in the range of −2 to 2, more preferably in the range of −1.5 to 1.5, the most preferably in the range of −1.5 to 0 or 1.1 to 1.5. Herein, the log P is a factor indicating an affinity of an organic compound to water and 1-octanol.

To be more concrete, there are preferably exemplified: ethanol, isopropanol, 2-phenoxyethanol, 2-benzyloxyethanol, diethyleneglycol monophenyl ether, triethyleneglycol monophenyl ether, tetraethyleneglycol monophenyl ether, 2-methyl-2,4-pentanediol, hexane-1,6-diol, nonane-1,6-diol, 2-propoxy-1-propanol, 2-methoxyethanol and the like.

While an amount of a solvent added is arbitrary, a less amount of the solvent added is desirable in order to raise a concentration of a sulfuric acid amine salt (I). The amount of the solvent is preferably 5 times or less as much as the amine (IV) by weight, more preferably 2 times or less. With an increased amount of a solvent added, a concentration of a sulfuric acid amine salt (I) is disadvantageously decreased. At a low temperature, on the other hand, the product itself is advantageously improved in quality and a lower storage temperature.

In a production process of the present invention, water can be further compounded when required. As water in use, there are exemplified: ion exchanged water at 60° C., distilled water, water containing a hypochlorite at a concentration of 10 mg/kg or less (for example, city water).

Although a neutralization compound of the compound (III) (such as sodium salt) and a neutralization compound of an amine (IV) (such as hydrochloride) are mixed with each other to obtain a sulfuric amine salt (I), this method has drawbacks described below.

i) In the case of an Na salt of the compound (III), it is difficult to achieve a compound with a high concentration of more than 5 wt % and at a higher concentration, a rapid increase viscosity make it difficult to neutralize. Therefore, an obtained sulfuric acid amine salt (I) has a low concentration and therefore cannot be compounded into an intended product as it is. A concentration is unavoidable.

ii) an inorganic salt such as NaCl is produced that has problems to adversely affect a physical property and to corrode a facility. The step of desalting is required and iii) the number of steps in production process increases.

A production process of the present invention has none of the above drawbacks, and to the contrary, has advantages shown bellow.

i) Since the compound (III) equal to or less than an amine (IV) in mole is added directly to the amine (IV) for neutralization, neutralization in a non-aqueous system makes it possible to thereby obtain a sulfuric acid amine salt (I) at a high concentration, ii) a sulfuric acid amine salt (I) that contains neither an Na salt nor a K salt can be obtained, iii) almost no increase in viscosity is observed in the case of a high concentration and neutralization at a low viscosity is enabled and iv) a process can be partly omitted.

A sulfuric acid amine salt (I) of the present invention shows a specific surface activity and is useful as a softener.

The composition of the present invention contains a sulfuric acid amine salt (I) and a solvent and is useful as a softener composition. A content of a sulfuric acid amine salt (I) in a composition of the present invention is preferably 10 wt % or more, more preferably 30 wt % or more and most preferably 50 wt % or more. A content of a solvent is preferably in the range of 0 to 90 wt %, more preferable in the range of 0 to 70 wt % and most preferably in the range of 0 to 50 wt %.

A sulfuric acid amine salt (I) of the present invention has a surface activity showing a specific behavior and is useful as a softener and a composition of the present invention is useful as a softener composition.

The compound (III') is represented by the formula $R^{51}$—$SO_3H$ (III') in which $R^{51}$ is a linear or branched $C_{12-36}$ alkyl or alkenyl group or an $C_{12-36}$ alkylaryl group. It can be obtained by sulfonating a compound having $R^{51}$—H (II') in a conventional way with a sulfonating agent. The amine salt (I') can be obtained from (III') in a similar way to (I).

[Component (a)]

In the compound represented by the formula (1) of the present invention, $R^1$ is an alkyl or alkenyl group having preferably 14 to 24 carbon atoms, more preferably 14 to 20 and most preferably 14 to 18 carbon atoms. $R^2$ is an alkylene group having preferably 2 or 3 carbon atoms. A is preferably —COO— or —CONH— and more preferably —CONH—. A small letter a is preferably 1. $R^3$ is preferably an alkyl group having 1 to 3 carbon atoms and more preferably a methyl group. $R^4$ is preferably an alkyl group having 1 to 3 carbon atoms and more preferably a methyl group. $R^5$ is an alkyl or alkenyl group having preferably 14 to 24 carbon atoms, more preferably 14 to 20 carbon atoms and most preferably 14 to 18 carbon atoms. $R^6$ is an alkylene group having preferably 2 or 3 carbon atoms. B is preferably —COO— or —CONH— and more preferably —CONH—. A small letter b is preferably 1.

As particularly preferable compounds among compounds represented by the formula (1), there are exemplified one or more kinds selected from the group consisting of compounds represented by the following formula (1-1) and compounds represented by the following formula (1-2).

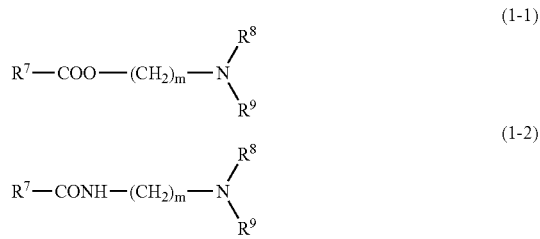

wherein $R^7$ is an alkyl or alkenyl group having 15 to 23 carbon atoms and preferably 15 to 19 carbon atoms, m is a number of 2 or 3, and each of $R^8$ and $R^9$ is a methyl or an ethyl group independently of the other and preferably a methyl group.

Compounds represented by the formulae (1-1) or (1-2) can be easily synthesized by reaction of a fatty acid represented by $R^7$—COOH, an alkyl ester thereof, wherein the alkyl group has 1 to 5 carbon atoms, or an acid chloride with N-hydroxyalkyl-N,N-dialkylamine or N-aminoalkyl-N,N-dialkylamine, wherein $R^7$ may be of either a single alkyl chain length or a mixed alkyl chain length.

[Component (b)]

A component (b) of the present invention is a compound with one $C_{12-36}$ hydrocarbon group and one group selected from the group consisting of —SO$_3$H and —OSO$_3$H each other, and to be concrete, there are preferably exemplified: an alkyl benzene sulfonic acid with a $C_{12-30}$ alkyl group, an alkyl (or alkenyl) sulfuric acid ester with a $C_{16-36}$ alkyl or alkenyl group, a polyoxyalkylenealkyl (or alkylenyl) ether sulfuric ester with a $C_{16-36}$ alkyl group (or an alkenyl group), and 1 to 4 oxyalkylene groups each having 2 to 3 carbon atoms, the number of added oxyalkylene groups being on the average, a $C_{12-30}$ olefin sulfonic acid, a $C_{12-30}$ alkane sulfonic acid, a $C_{12-30}$ α-sulfo fatty acid, and $C_{12-30}$ α-sulfo fatty acid ester.

The hydrocarbon group of the component (b) is preferably a branched alkyl or alkenyl group including 1 to 5 carbon atoms bonding to 3 to 4 carbon atoms from the viewpoint of softening effect. Such hydrocarbon groups are preferably exemplified by a Guerbet alkyl group, an isostearyl group or an isostearic acid residual group. In addition, it preferably includes a polymethyl branched alkyl group derived by removing hydroxy group from an alcohol obtained by producing an aldehyde by oxo-reaction of a tetramer, a pentamer or a hexamer of butene, followed by hydrogenation. It may include also a polymethyl branched alkyl group derived by removing —COOH from a fatty acid obtained by oxidation of the alcohol described above. A $C_{16-36}$ Guerbet alkyl group is the most preferable, in particular a $C_{18-28}$ Guerbet alkyl group, from the view point of a softening effect.

As components having a Guerbet alkyl group, there are preferably exemplified: a $C_{16-36}$ Guerbet alkyl group sulfuric ester with an alkyl group, preferably $C_{18-28}$, and a polyoxyalkylene Guerbet alkyl ether sulfuric acid ester with an alkylene group having 2 and/or 3 carbon atoms, oxyalkylene groups an average number of moles added of which is a number of from 1 to 4 in the polyoxyalkylene part and an alkyl group having 16 to 36 carbon atoms and preferably 18 to 28 carbon atoms in the Guerbet alkyl part.

In the process for producing a branched alcohol used for the starting material of such a compound, Guerbet reaction may be performed between an aldehyde and an alkali to obtain a primary alcohol at the second position of which an alkyl group is branched. Alternatively a branched alcohol or the like can be obtained by dehydrogenating an alcohol with a Ni catalyst or the like to prepare a corresponding aldehyde and subjecting the aldehyde to Guerbet reaction and then hydrogenation.

In the present invention, there can also be used a branched alkyl sulfuric acid ester obtained by sulfating such a branched alcohol with SO$_3$, chlorosulfonic acid or the like. Furthermore, there can be used a polyoxyethylene (and/or propylene) branched chain alkyl ether sulfuric acid ester obtained by sulfating such a polyoxyethylene (and/or propylene) branched chain alkyl ether with SO$_3$, chlorosulfonic acid or the like.

In the present invention, a most preferable (b) component is a compound represented by the following formula (2).

$$R^{10}—(OR^{11})_n—OSO_3H \qquad (2)$$

wherein $R^{10}$ is a $C_{16-36}$ branched alkyl or alkenyl group including 1 to 5 carbon atoms bonding to 3 to 4 carbon atoms, preferably being $C_{18-28}$, $R^{11}$ is an ethylene group or a propylene group, and n is a number of from 0 to 4, preferably a number of from 0 to 2 and most preferably a number of 0.

[Step A]

Step A is a step of mixing a component (a) and a component (b) in advance to a obtain a surfactant mixture. In Step A, while a component (a) in the surfactant mixture may be either the whole of the component (a) used in a softener composition or part thereof, the whole of the (b) component used in a softener composition is preferably contained in the surfactant mixture. A mass ratio of a component (a) to a component (b) ((a)/(b)) in a surfactant mixture is preferably in the range of 99/1 to 40/60, more preferably in the range of 95/5 to 50/50, especially preferably 90/10 to 52/48, the most preferably in the range of 85/15 to 60/40.

In Step A, an organic solvent (component (c)) is preferably mixed into the surfactant mixture for the purpose of suppressing increase in viscosity and gelation during production.

The compound (c) is an organic solvent having log P of 0.5 to 3, preferably 0.5 to 2, more preferably 0.8 to 1.8, the most preferably 1.1 to 1.6.

The log P is a factor indicating an affinity of an organic compound to water and 1-octanol. The 1-octanol/water distribution coefficient P is the ratio of the equilibrium concentrations of a compound in the respective solvents in the state of distribution equilibrium when a small amount of the compound is dissolved as a solute in a solvent mixture of two phases consisting of 1-octanol and water and is generally expressed in the form of logarithmic value of the ratio, namely, log P to the base 10. Values of log P of many compounds have been reported and many values are stored for reference in a data base obtainable from Daylight Chemical Information Systems, Inc. (Daylight CIS) or the like. In the case where no actually measured value of log P is available, it is most convenient to calculate with a program "CLOGP" obtainable from Daylight CIS. This program, in the case where an actually measured value of log P is available, outputs a calculated value of log P (Clog P) calculated through a fragment approach of Hansch and Leo together with the actually measured value. This Fragment Approach is based on the chemical structure of a compound and takes the number of atoms and the type of chemical bond into account (cf. A. Leo, Comprehensive Medicinal Chemistry, Vol. 4, C. Hansch, P. G. Sammens, J. B. Taylor and C. A. Ramsden, Eds., p. 295, Pergamon Press, 1990). Since a value of Clog P is a currently most commonly used and reliable estimate, this value can be used in selection of a compound instead of an actually measured value of log P. In the present invention, an actually measured value of log P was used if available, while using a calculated value Clog P obtained by calculation according to the program CLOGP version 4.01 unless available.

As organic solvents having such values of log P, there are preferably exemplified compounds represented by the following formulae (3), (4) or (5).

$$R^{12}\text{—OH} \quad (3)$$

wherein $R^{12}$ is a $C_{4-8}$ hydrocarbon group, preferably an alkyl group, an aryl group or an arylalkyl group.

$$R^{13}\text{—(O—}R^{14})_g\text{—O—}R^{15} \quad (4)$$

wherein each of $R^{13}$ and $R^{15}$ is a hydrogen atoms, $R^{16}CO\text{—}$ (wherein $R^{16}$ is a $C_{1-3}$ alkyl group) or a $C_{1-7}$ hydrocarbon group, preferably being a hydrogen atom, an alkyl group, an aryl group or an arylalkyl group, and $R^{14}$ is an alkylene group which may have a branched chain having 2 to 9 carbon atoms. Note that cases are excluded where $R^{14}$ is a $C_{2-3}$ alkylene group and $R^{13}$ and $R^{15}$ are both a hydrogen atom. A small letter of g is a number of from 1 to 5.

$$R^{17}\text{—O—}CH_2CH(\text{O—}R^{18})CH_2\text{—O—}R^{19} \quad (5)$$

wherein in the formula, $R^{17}$ is a $C_{3-8}$ alkyl group and each of $R^{18}$ and $R^{19}$ is, independently the other, a hydrogen atom or a $C_{1-3}$ alkyl group, which may be substituted with a hydroxy group.

As more preferable concrete compounds, there can be exemplified: n-butanol, isobutanol, 2-butanol, n-hexanol, cyclohexanol, phenol, benzyl alcohol, phnethyl alcohol, 2-phenoxyethanol, 2-benzyloxyethanol, diethyleneglycol monobenzyl ether, diethyleneglycol monophenyl ether, triethylenglycol monophenyl ether, tetraethyleneglycol monophenyl ether, 2-ethylhexane-1,3-diol, hexane-1,6-diol, nonane-1,6-diol, 2-methyloctane-1,8-diol, 2-butoxyethanol, diethyleneglycol monobutyl ether, propyleneglycol monobutyl ether, propyleneglycol monophenyl ether, triethyleneglycol monobutyl ether, 2-(2-methyl)propoxyethanol, diethyleneglycol mono-2-methylpropyl ether, 2-propoxy-1-propanol, dipropyleneglycol monopropyl ether, 2-butoxy-1-propanol, dipropyleneglycol monobutyl ether, 2-t-butoxy-1-propanol, 2-phenoxy-1-propanol, 2-ethoxypropyl-1-acetate, 2-propoxypropyl-1-acetate, 1,2-diacetoxypropane, 3-dimethyl-3-methoxy-1-propanol, 1,3-dimethylbutylglyceryl ether, pentylglyceryl ether and hexylglyceryl ether.

Among them, particularly preferable are n-hexanol, benzyl alcohol, 2-phenoxyethanol, 2-benzyloxyethanol, propyleneglycol monobutyl ether, propyleneglycol monophenyl ether, hexylglyceryl ether, diethyleneglycol monobutyl ether, diethylglycol monophenyl ether, triethylenglycol monophenyl ether, tetraethyleneglycol monophenyl ether, hexane-1,6-diol, nonane-1,6-diol, 2-propoxy-1-propanol and dipropyleneglycol monopropyl ether, and a most preferable component (c) from the view point of suppression of increase in viscosity and gelation during production is one or more kinds selected from the group consisting of 2-phenoxyethanol, diethylglycol monophenyl ether and triethylenglycol monophenyl ether.

A surfactant mixture of the present invention can contain part or the whole of a component (c) used in a softener composition. A content of a component (c) in a surfactant mixture is preferably in the range of 5 to 60 mass %, more preferably in the range of 10 to 50 mass % and most preferably in the range of 15 to 40 mass %.

As methods for mixing a component (a), a component (b) and a component (c) with each other, there are exemplified: a method for mixing the three components simultaneously, a method in which two components are mixed while a residual component is added, a method in which after two components are mixed in advance, the residual component is mixed into the mixture, and a method obtained by combining the methods, but no specific limitation is placed on the methods described above. A preferable method is to mix a component (b) into a mixture of a component (a) and a component (c), in which case, a heat generation accompanies mixing, so mixing is preferably performed while cooling.

As a method of preparing a compound represented by the formula (2) as a component (b), a method is preferable in which an alcohol represented by the formula (6):

$$R^{10}\text{—(O}R^{11})_n\text{—OH} \quad (6)$$

wherein $R^{10}$, $R^{11}$ and n show the same meanings as in the above description, is sulfated by means of a common sulfation method using $SO_3$ gas diluted with dry air or inert gas in a thin film continuous sulfation facility, the gas and a sulfated compound are separated with a cyclone, immediately thereafter, the sulfated compound is mixed into the component (a) (if the component (a) is in a solid state, it is preheated into a molten state) and preferably into the component (a) and the component (c) for neutralization. A reaction temperature in sulfation is preferably in the range of 20 to 80° C. A reaction molar ratio between an alcohol represented by the formula (6) and $SO_3$ gas reaction, alcohol/$SO_3$, is preferably in the range of 0.80 to 1.20.

In order to increase a compatibility of a component (c) with a component (a) or a component (b) in Step A and to accelerate a dispersion speed of a surfactant mixture into water in Step B, water as a component (d) is preferably mixed into the system. While a component (d) maybe mixed into a component (a), a component (b) or a component (c), it is preferable to mix the component (d) into a surfactant mixture. A mass ratio of the component (d) to the sum of the component (a) and the component (b) (component (d)/(component (a)+component (b)), is preferably in the range of 0.5/99.5 to 20/80, more preferably 5/95 to 20/80.

[Step B]

Step B is a step of dissolving and/or dispersing a surfactant mixture obtained in Step A into water (hereinafter referred to as a component (e)). In Step B, it is preferable to add the molten surfactant mixture into water at a temperature in the range of 20 to 100° C., preferably in the range of 25 to 80° C., more preferably in the range of 30 to 80° C. and further more preferably in the range of 40 to 70° C.

A mass ratio of the sum of the component (a) and the component (b) to the component (e) in the surfactant mixture, [component (a)+component (b)]/component (e)], is preferably in the range of 5/95 to 50/50, more preferably in the range of 10/90 to 50/50 and most preferably in the range of 10/90 to 40/60.

When the surfactant mixture is added into water, agitation may be performed or the agitation may be ceased during addition, followed by agitation after the addition ends. A shearing speed Φ of an agitation blade during agitation is represented by the formula (7):

$$\Phi = \pi \cdot n \tag{7}$$

wherein in the formula, Φ is a shearing speed [sec$^{-1}$], π is a circle ratio and n indicates a rotation number of the agitation blade [sec$^{-1}$], wherein Φ is preferably in the range of 1 to 3000 sec$^{-1}$ and particularly preferably in the range of 3 to 1500 sec$^{-1}$. Agitation is performed either continuously or intermittently.

[Softener Composition]

In a softener composition according to the present invention, it is preferable to add a nonionic surfactant as a component (f) from the viewpoint of suppression of gelation during production and storage stability. The nonionic surfactant is preferably exemplified by polyoxyethylenealkyl ether with a $C_{8-20}$ alkyl or alkenyl group and/or a compound obtained by adding an alkylene oxide to fat and oil or a partial hydrolyzed compound thereto. As a particularly preferable example of polyoxyethylenealkyl ether with a $C_{8-20}$ alkyl or alkenyl group, there is exemplified a nonionic surfactant represented by the following formula (8). As particularly preferable examples of a compound obtained by adding an alkylene oxide to fat and oil or a partial hydrolyzed compound thereto, there are exemplified: a polyoxyalkylene adduct of a hardened castor oil (an average number of moles added is preferably in the range of 30 to 100, more preferably in the range of 50 to 80.

$$R^{20}\text{-M-}[(R^{21}O)_h\text{—}R^{22}]_i \tag{8}$$

wherein $R^{20}$ is an alkyl or alkenyl group having 8 to 18 carbon atoms and preferably 10 to 16 carbon atoms and $R^{21}$ is an alkylene group having 2 or 3 carbon atoms, preferably an ethylene group. $R^{22}$ is a $C_{1-3}$ alkyl group or a hydrogen atom. A small letter h indicates a number of 2 to 100, preferably a number 5 to 80, more preferably a number of 5 to 60 and most preferably a number of 10 to 40. M is —O—, —COO—, —CON— or —N— and in the case where M is —O— or —COO—, i is 1, while in the case where M is —CON— or —N—, i is 2. Herein, a plurality of $R^{21}$ may be different from or the same as one another, alternatively being a mixture of alkylene groups having 2 and 3 carbon atoms, respectively. A plurality of $R^{22}$ may be different from or the same as one another.

As concrete examples of the compound represented by the formula (8), there are exemplified: compounds represented by the following formulae (8-1) to (8-4):

wherein in the formula, $R^{20}$ indicates the meaning in the above description and j is a number of 8 to 100 and preferably a number of 10 to 60.

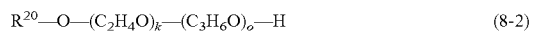

wherein in the formula, $R^{20}$ indicates the meaning in the above description, each of k and o is a number of from 2 to 40 and preferably a number of 5 to 40 independently of the other, and $(C_2H_4O)$ and $(C_3H_6O)$ each may be either a random adduct or a block adduct.

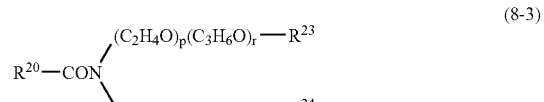

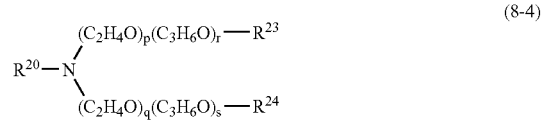

wherein in the formula, $R^{20}$ indicates the meaning in the above description, each of p, q, r and s is a number of 0 to 40 independently of the other, p+q+r+s is a number of 5 to 60 and preferably a number of from 5 to 40, and $(C_2H_4O)$ and $(C_3H_6O)$ each may be either a random adduct or a block adduct. Each of $R^{23}$ and $R^{24}$ is a hydrogen atom or an alkyl group having 1 to 3 carbon atoms independently of the other.

A softener composition according to the present invention can contain an inorganic salt as a component (g). As inorganic salts, there are preferably exemplified: sodium chloride, calcium chloride and magnesium chloride from the viewpoint of storage stability. However, while a sodium salt and a potassium salt are contained in a surfactant such as fatty acid salts, none of the above described limitation is imposed on the inorganic salts mixed into the composition when such surfactants are used.

A softener composition according to the present invention can contain an ester compound of saturated or unsaturated fatty acid having 8 to 22 carbon atoms and polyvalent alcohol as a component (h) for the purpose of improving hand touch feeling of clothes without any problem. As compounds (h), there can be exemplified: a triglyceride, a diglyceride, a monoglyceride, mono, di, and trimesters of pentaerythritol and a sorbitan ester.

A softener composition according to the present invention can contain a sequestering agent and an antioxidant, which are commonly known, (hereinafter referred to as a component (i)) for the purpose of improving a color and a smell after storage. As sequestering agents, there can be exemplified amino carboxylic acids represented by an ethylene diamine tetra acetic acid salt, a diethylene triamine penta acetic acid salt, and the like, inorganic phosphorus compounds represented by a tripoly phosphoric acid salt and a pyrophosphoric acid salt and organophosphoric acids represented by 1-hydroxyethane-1, a 1-diphosphonic acid salt, polyphosphonic acids and phytic acid. The compound described above may be compounded as an acid or a salt. As antioxidants, there are exemplified: 2,6-di-tert-butyl-4-methylphenol, 2(3)-butyl-4-oxyanisole and the like.

A softener composition according to the present invention can preferably contain an organic acid (hereinafter referred to as a component (j)), of a melting point (mp) of 25° C. or higher, preferably in the range of 50 to 300° C. and more preferably in the range of 50 to 200° C., and with a hydrocarbon group having 1 to 10 carbon atoms and preferably 1 to 7 carbon atoms from the viewpoint of an effect of suppressing deterioration of a smell. As actual, preferable compounds, there can be exemplified: glycolic acid (mp 80° C.), oxalic acid (mp 102° C.), lactic acid (mp 26° C.), malonic acid (mp 135° C.), succinic acid (mp 185° C.), maleic acid (mp 130° C.), malic acid (mp 100° C.), tartaric acid (mp 170° C.), glutaric acid (mp 98° C.), adipic acid (mp 153° C.), n-butylmalonic acid (mp 102° C.), azelaic acid (mp 107° C.), citric acid (mp 153° C.), benzoic acid (mp 122° C.) and phthalic acid (mp 191° C.). Particularly preferable among them are glycolic acid, citric acid, oxalic acid and lactic acid from the viewpoint of an effect of suppressing deterioration of a smell.

A softener composition according to the present invention can preferably contain a perfume commonly used as a fiber treatment agent (particularly preferable is a combination of aromatic components shown as components (c) and (d) described in JP-A No. 8-113871), a colorant or the like without causing a problem.

Though the above described components (f) to (j) may be compounded in any step, the components are preferably compounded after Step B or prior to Step B.

A content of a component (a) in a softener composition according to the present invention is preferably in the range of 3 to 50 mass %, more preferably in the range of 3 to 35 mass % and most preferably in the range of 4 to 30 mass %. Furthermore, proportions of a component (a) and a component (b) ((a)/(b) of molar ratio) are in the range of 9/1 to 4/6, more preferably in the range of 9/1 to 5/5 and most preferably in the range of 8.5/1.5 to 6.5/3.5 from the viewpoint of a softening effect. A content of a component (c) is preferably in the range of 3 to 40 mass %, more preferably in the range of 5 to 30 mass % and most preferably in the range of 10 to 25 mass % from the viewpoint of compoundability. A content of water is preferably in the range of 30 to 90 mass %, more preferably in the range of 30 to 80 mass % and most preferably in the range of 40 to 70 mass %. Water may be added to a composition at a later step in addition to a component (d) and a component (e). A content of a component (f) is preferably in the range of 0.1 to 10 mass %, more preferably in the range of 0.2 to 5 mass % and most preferably in the range of 1 to 5 mass % from the viewpoint of suppression of gelation during production. A content of a component (g) is preferably in the range of 0.05 to 10 mass %, more preferably in the range of 0.05 to 2 mass % and most preferably in the range of 0.05 to 0.45 mass % from the viewpoint of storage stability. A content of a component (h) is preferably in the range of 0.2 to 10 mass %, more preferably in the range of 0.5 to 5 mass % and most preferably in the range of 0.5 to 3 mass % from the viewpoint of improvement on hand touch feeling. A content of a component (i) is preferably in the range of 2 to 5000 mg/kg, more preferably in the range of 10 to 1000 mg/kg and most preferably in the range of 100 to 500 mg/kg from the viewpoint of improvement on a color and a smell. Furthermore, a content of a component (j) is preferably in the range of 0.1 to 10 mass %, more preferably in the range of 0.2 to 5 mass % and most preferably in the range of 0.3 to 3 mass % from the viewpoint of suppression of an unpleasant odor.

According to the process for production of the present invention, a softener composition can be produced that contains an amine compound and an anionic surfactant without causing increase in viscosity or generation and an obtained softener composition can sufficiently exert a softening effect.

Detailed description will be given to the present invention based on Examples 1 to 7 and 11 to 17 below.

A symbol % in the examples is wt %, unless otherwise specified.

EXAMPLE 1

In a continuous thin film reactor, 5307 g of a sulfated compound obtained by sulfating 2-decyl-tetradecylalcohol (hereinafter referred to as $C_{24}$ Guerbet alcohol) with $SO_3$ gas was poured, for neutralization, into 5574 g of 3-octadecanoyl amidopropyl(N,N-dimethyl)amine (hereinafter referred to as $C_{18}APA$) in a molten state at 80° C. to obtain a brownish transparent liquid (in a solid state at room temperature with a melting point of 45° C.)

According to the following IR and $^1$H-NMR analyses, it was confirmed that the obtained brownish transparent liquid was a mixture of 89.4% of a compound represented by the formula (I-1) and 10.6% of free amine (as $C_{18}APA$).

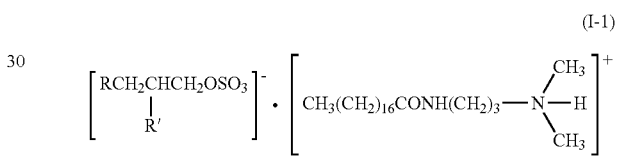

(I-1)

wherein R indicates an alkyl group having 11 carbon atoms and R' indicates an alkyl group having 10 carbon atoms.

<IR Analysis>

A strong absorption was recognized at 1660 cm$^{-1}$ special to an amide.

A strong absorption was recognized at 1220 and 1470 cm$^{-1}$ special to a sulfuric acid salt.

<$^1$H-NMR Analysis>

Measurements were performed in a solvent of CDCl$_3$ with TMS as an internal standard.

2.88 ppm (C$\underline{H}_3$)$_2$N$^+$H— (6H)
3.13 ppm >N$^+$—C$\underline{H}_2$—CH$_2$—CH$_2$—NHCO (2H)
1.61 ppm >N$^+$—CH$_2$—C$\underline{H}_2$—CH$_2$—NHCO (2H)
3.38 ppm >N$^+$—CH$_2$—CH$_2$—C$\underline{H}_2$—NHCO (2H)
2.22 ppm —NHCOC$\underline{H}_2$— (2H)
3.96 ppm —C$\underline{H}'_2$—O—SO$_3$— (2H)

EXAMPLE 2

In a continuous thin film reactor, 159 g of a sulfated compound obtained by sulfating 2-octyl-dodecylalcohol with $SO_3$ gas was poured, for neutralization, into 193 g of $C_{18}APA$ while agitating in a molten state at 80° C. to obtain a brownish transparent liquid (in a solid state at room temperature with a melting point of 40° C.).

According to the following IR and $^1$H-NMR analyses, it was confirmed that the obtained brownish transparent liquid was a mixture of 94.0% of a compound represented by the formula (I-2) and 6.0% of free amine ($C_{18}APA$).

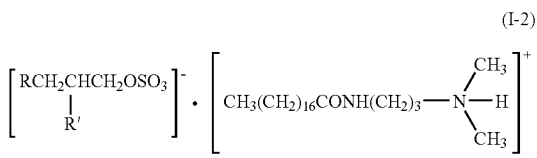

(I-2)

wherein in the formula, R indicates an alkyl group having 9 carbon atoms and R' indicate an alkyl group having 8 carbon atoms.

<IR Analysis>

A strong absorption was recognized at 1660 cm$^{-1}$ special to an amide.

A strong absorption was recognized at 1220 and 1470 cm$^{-1}$ special to a sulfuric acid salt.

<$^1$H-NMR Analysis>

Measurements were performed in a solvent of CDCl$_3$ with TMS as an internal standard.

2.88 ppm (C$\underline{H}_3$)$_2$N$^+$H— (6H)
3.13 ppm >N$^+$—C$\underline{H}_2$—CH$_2$—CH$_2$—NHCO (2H)
1.61 ppm >N$^+$—CH$_2$—C$\underline{H}_2$—CH$_2$—NHCO (2H)
3.38 ppm >N$^+$—CH$_2$—CH$_2$—C$\underline{H}_2$—NHCO (2H)
2.22 ppm —NHCOC$\underline{H}_2$— (2H)
3.96 ppm —C$\underline{H}_2$—O—SO$_3$— (2H)

EXAMPLE 3

In a continuous thin film reactor, 175 g of a sulfated compound obtained by sulfating stearyl alcohol with SO$_3$ gas was poured, for neutralization, into 193 g of C$_{18}$APA while agitating in a molten state at 80° C. to obtain a brownish transparent liquid (in a solid state at room temperature with a melting point of 95° C.)

According to the following IR and $^1$H-NMR analyses, it was confirmed that the obtained brownish transparent liquid was a mixture of 97.2% of a compound represented by the formula (I-3) and 2.8% of free amine (C$_{18}$APA).

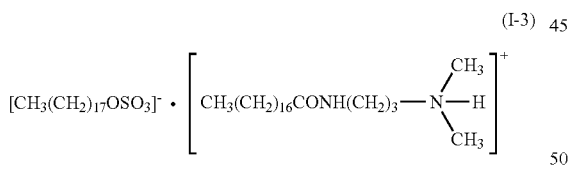

(I-3)

<IR Analysis>

A strong absorption was recognized at 1660 cm$^{-1}$ special to an amide.

A strong absorption was recognized at 1220 and 1470 cm$^{-1}$ special to a sulfuric acid salt.

<$^1$H-NMR Analysis>

Measurements were performed in a solvent of CDCl$_3$ with TMS as an internal standard.

2.90 ppm (C$\underline{H}_3$)$_2$N$^+$H— (6H)
3.16 ppm >N$^+$—C$\underline{H}_2$—CH$_2$—CH$_2$—NHCO (2H)
1.67 ppm >N$^+$—CH$_2$—C$\underline{H}_2$—CH$_2$—NHCO (2H)
3.38 ppm >N$^+$—CH$_2$—CH$_2$—C$\underline{H}_2$—NHCO (2H)
2.22 ppm —NHCOC$\underline{H}_2$— (2H)
4.03 ppm —C$\underline{H}_2$—O—SO$_3$— (2H)

EXAMPLE 4

In a continuous thin film reactor, 141 g of a sulfated compound obtained by sulfating C$_{24}$ Guerbet alcohol with SO$_3$ gas was poured, for neutralization, into a mixture of 150 g of C$_{18}$APA and 150 g of 2-phenoxyethanol while agitating in a molten state at 50° C. to obtain a transparent liquid in light brown color.

The obtained transparent liquid in light brown color was a mixture of 54.9% of a compound represented by the formula (I-1), 11.1% of free amine (C$_{18}$APA) and 34.0% of 2-phenoxyethanol.

EXAMPLE 5

In a continuous thin film reactor, 141 g of a sulfated compound obtained by sulfating C$_{24}$ Guerbet alcohol with SO$_3$ gas was poured, for neutralization, into a mixture of 150 g of C$_{18}$APA and 150 g of ethanol while agitating in a molten state at 50° C. to obtain a transparent liquid in light brown color.

The obtained transparent liquid in light brown color was a mixture of 58.7% of a compound represented by the formula (I-1), 7.3% of free amine (C$_{18}$APA) and 34.0% of ethanol.

EXAMPLE 6

In a continuous thin film reactor, 140 g of a sulfated compound obtained by sulfating C$_{24}$Guerbet alcohol with SO$_3$ gas was poured, for neutralization, into 150 g of 2-dimethylamino-N-octadecyl-acetoamide while agitating in a molten state at 80° C. to obtain a brownish transparent liquid (in a solid state at room temperature).

The obtained transparent liquid in light brown color was a mixture of 87.0% of a compound represented by the formula (I-4) and 13.0% of free amine (2-dimethylamino-N-octadecyl-acetoamide).

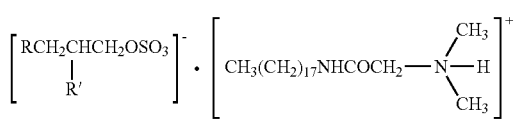

(I-4)

wherein in the formula, R indicates an alkyl group having 11 carbon atoms and R' indicates an alkyl group having 10 carbon atoms.

EXAMPLE 7

In a continuous thin film reactor, 140 g of a sulfated compound obtained by sulfating C$_{24}$ Guerbet alcohol with SO$_3$ gas was poured, for neutralization, into 150 g of octadecanoic acid dimethylaminomethyl ester while agitating in a molten state at 80° C. to obtain a brownish transparent liquid (in a solid state at room temperature).

The obtained brownish transparent liquid was a mixture of 86.9% of a compound represented by the formula (I-5) and 13.1% of free amine (octadecanoic acid dimethylaminomethyl ester).

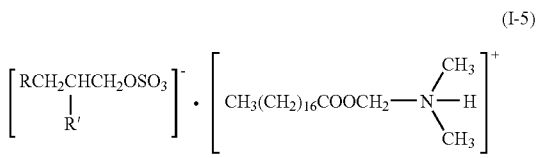

(I-5)

wherein in the formula, R indicates an alkyl group having 11 carbon atoms and R' indicates an alkyl group having 10 carbon atoms.

EXAMPLE 11

Sulfation of 2-decyl-1-tetra decanol (which was obtained by a Guerbet reaction of lauryl aldehyde) is performed with SO$_3$ to obtain a sulfated compound.

The above sulfated compound in amount of 96 g was poured into a solution obtained by agitating to mix 102 g of N-(3-stearoylaminopropyl)-N,N-dimethyl amine and 102 g of 2-phenoxyethanol with each other at 50° C. while cooling with a water bath (at a water temperature of 20° C.). Agitation was continued for 10 min. to obtain a surfactant mixture in light brown color.

Then, in a beaker of 1000 ml with two sets of 3 agitating blades of 3.5 cm in diameter at respective two blade positions 1.5 cm and 4 cm from the bottom of the beaker, 450 g of ion exchanged water was put and 300 g of the surfactant mixture obtained in the above process was added into the ion exchanged water over 15 sec. while agitating the ion exchanged water at 200 r/min. After the addition, the compounded material was further agitated for 3 min. Thereafter, a pH value of the compounded material was adjusted with a 6 N hydrochloric acid solution to 4.5, followed by agitation for another 2 min. Then, ion exchanged water was added into the compounded material so as to be 800 g in amount and thereafter, the compounded material was cooled down to 30° C. while agitating in a water bath at 20° C. to obtain a softener composition A.

Note that in the example, absolutely neither increase in viscosity nor gelation was observed during production.

EXAMPLE 12

A softener composition B was obtained absolutely in the same way as in Example 11 with the exception that N-[2-beef tallow fatty acid (composed of stearic acid/palmitic acid=60/40) alkanoyloxyethyl]-N,N-dimethyl amine was substituted for N-(3-stearoylaminopropyl)-N,N-dimethyl amine.

Note that in the example, absolutely neither increase in viscosity nor gelation was observed during production.

EXAMPLE 13

A softener composition C was obtained absolutely the same way as in Example 11 with the exception that N,N-di [2-beef tallow fatty acid (composed of stearic acid/palmitic acid=60/40) alkanoyloxyethyl]-N-methyl amine was substituted for N-(3-stearoylaminopropyl)-N,N-dimethyl amine.

Note that in the example, absolutely neither increase in viscosity nor gelation was observed during production.

EXAMPLE 14

A softener composition D was obtained absolutely the same way as in Example 11 with the exception that a compound obtained by adding 3 moles on the average of ethylene oxide to 2-octyl-1-dodecanol was substituted for 2-decyl-1-tetra decanol.

Note that in the example, absolutely neither increase in viscosity nor gelation was observed during production.

EXAMPLE 15

A sulfated compound was obtained by sulfating 2-decyl-1-tetra decanol (which was obtained by a Guerbet reaction of lauryl aldehyde) with SO$_3$ gas.

The above sulfated compound in amount of 96 g was poured into a solution obtained by agitating to mix 102 g of N-(3-stearoylaminopropyl)-N,N-dimethyl amine and 102 g of 2-phenoxyethanol with each other at 50° C. while cooling in a water bath (at a water temperature of 20° C.). Then, 30 g of ion exchanged water was poured into the mixture. Agitation was continued for 10 min. to obtain a surfactant mixture in light brown color.

Then, in a beaker of 1000 ml with two sets of 3 agitating blades of 3.5 cm in diameter at two blade positions 1.5 cm and 4 cm from the bottom of the beaker, 450 g of ion exchanged water was put and 330 g of the surfactant mixture was added into the ion exchanged water over 15 sec. while agitating the ion exchanged water at 200 r/min. After the addition, the compounded material was further agitated for 3 min. Thereafter, a pH value of the compounded material was adjusted with a 6 N hydrochloric acid solution to 4.5, followed by agitation for another 2 min. Then, ion exchanged water was added into the compounded material so as to be 800 g in amount and thereafter, the compounded material was cooled down to 30° C. while agitating in a water bath at 20° C. to obtain a softener composition E.

Note that in the example, absolutely neither increase in viscosity nor gelation was observed during production.

EXAMPLE 16

A surfactant mixture in light brown color was obtained in a similar method to Example 11. Then, in a beaker of 1000 ml with two sets of 3 agitating blades of 3.5 cm in diameter at two blade positions 1.5 cm and 4 cm from the bottom of the beaker, 450 g of ion exchanged water was put and 300 g of the surfactant mixture obtained in the above process was added into the ion exchanged water over 15 sec. while agitating the ion exchanged water at 200 r/min. After the addition, the compounded material was further agitated for 3 min. Thereafter, the following compounds were sequentially added in the order: 24 g of an ethylene oxide adduct (an average number of moles added is 20) to lauryl alcohol melted at 60° C., 4.8 g of 50% magnesium chloride aqueous solution, 0.58 g of pentaerythritol monostearate melted at 80° C., 0.5 g of a 10% ethanol solution of 2,6-di-tert-butyl-4-methylphenol and 10 g of a 50% citric acid aqueous solution. After the addition, the compounded material was agitated for 5 min. Thereafter, a pH value of the compounded material was adjusted with a 6 N hydrochloric acid solution to 4.5, followed by agitation for another 2 min. Then, ion exchanged water was added into the compounded material so as to be 800 g in amount and thereafter, the compounded material was cooled down to 30° C. while agitating in a water bath at 20° C. to obtain a softener composition F.

Note that in the example, absolutely neither increase in viscosity nor gelation was observed during production.

EXAMPLE 17

A surfactant mixture in light brown color was obtained in a similar method to Example 11. Then, in a beaker of 1000 ml with two sets of 3 agitating blades of 3.5 cm in diameter at two blade positions 1.5 cm and 4 cm from the bottom of the beaker, 450 g of ion exchanged water was put and the following chemical compounds were sequentially added in the order while agitating the ion exchanged water at 200 r/min: 24 g of an ethylene oxide adduct (an average number of moles added is 70) to hardened castor oil melted at 60° C., 4.8 g of 50% magnesium chloride aqueous solution, 0.27 g of a 30% aqueous solution of sodium ethylene diamine tetra acetate and 10 g of a 50% citric acid aqueous solution and thereafter, 300 g of the surfactant mixture obtained in the above process was added over 15 sec. After the addition, the compounded material was agitated for 3 min. Thereafter, a pH value of the compounded material was adjusted with a 6 N hydrochloric acid solution to 4.5, followed by agitation for another 2 min. Then, ion exchanged water was added into the compounded material so as to be 800 g in amount and thereafter, the compound was cooled down to 30° C. in a water bath at 20° C. to obtain a softener composition G. Note that in the example, absolutely neither increase in viscosity nor gelation was observed during production.

COMPARATIVE EXAMPLE 1

A solution obtained by agitating to mix 102 g of N-(3-stearoylaminopropyl)-N,N-dimethyl amine and 102 g of 2-phenoxyethanol with each other at 50° C. is added into 450 g of ion exchanged water at 60° C. contained in a beaker of 1000 ml with two sets of 3 agitating blades of 3.5 cm in diameter at two blade positions 1.5 cm and 4 cm from the bottom of the beaker over 15 seconds, while agitating the ion exchanged water at 200 r/min. Then, 96 g of a sulfated product at 50° C. obtained by sulfating 2-decyl-1-tetra decanol (which was obtained by a Guerbet reaction of lauryl aldehyde) with $SO_3$ gas was added over 15 sec. into the compounded material and after addition, the agitation is continued for 3 min. Thereafter, a pH value of the compounded material was adjusted with a 6 N hydrochloric acid solution to 4.5, followed by agitation for another 2 min. Then, ion exchanged water was added into the compounded material so as to be 800 g in amount and thereafter, the compounded material was cooled down to 30° C. while agitating with a water bath at 20° C. to obtain a softener composition H.

Note that a viscosity is drastically raised while the sulfated product obtained by sulfating 2-decyl-1-tetra decanol was added during the above production. After compounding as well, oily drops in light yellow color are present inhomogeneously, which was estimated as N-(3-stearoylaminopropyl)-N,N-dimethyl amine.

COMPARATIVE EXAMPLE 2

A softener composition I was obtained in absolutely the same way as in Comparative Example 1 with the exception that N-[2-beef tallow fatty acid (composed of stearic acid/palmitic acid=60/40) alkanoyloxyethyl]-N,N-methyl amine was substituted for N-(3-stearoylaminopropyl)-N,N-dimethyl amine.

Note that in the comparative example, viscosity is drastically raised while the sulfated product obtained by sulfating 2-decyl-1-tetra decanol was added. After compounding as well, oily drops in light yellow color are present inhomogeneously.

COMPARATIVE EXAMPLE 3

A solution obtained by agitating to mix 102 g of N-(3-stearoylaminopropyl)-N,N-dimethyl-amine and 102 g of 2-phenoxyethanol with each other at 50° C. is added into 450 g of ion exchanged water at 60° C. contained in a beaker of 1000 ml with two sets of 3 agitating blades of 3.5 cm in diameter at two blade positions 1.5 cm and 4 cm from the bottom of the beaker over 15 sec. while agitating the ion exchanged water at 200 r/min. Then, 96 g of a sulfated product at 50° C. obtained by sulfating 2-decyl-1-tetra decanol (which was obtained by a Guerbet reaction of lauryl aldehyde) with $SO_3$ gas was added over 15 sec. while agitating the compounded material and after addition, the agitation is continued for 3 min. Thereafter, a pH value of the compounded material was adjusted with a 6 N hydrochloric acid solution to 4.5, followed by agitation for another 2 min and then, ion exchanged water was added into the compounded material so as to be 800 g in amount. In compounding, viscosity is drastically raised while the sulfated product obtained by sulfating 2-decyl-1-tetra decanol was added and oily drops in light yellow color were present inhomogeneously which was estimated as N-(3-stearoylaminopropyl)-N,N-dimethyl amine; therefore, the compounded material was agitated for 2 min at 500 r/min with an auto-homomixer M model made by Tokushu Kika K.K. and thereafter, the compounded material was cooled down to 30° C. while agitating in a water bath at 20° C. to obtain a softener composition J. In the softener composition J, an oil phase in liquid yellow was observed.

TEST EXAMPLE

A softening treatment was performed using softener compositions obtained in the examples and the comparative examples according to the following method to evaluate a softening property. Results are shown in Table 1.

<Softening Treatment Method>

Five bath towels made from 100% cotton were washed using a weak alkaline detergent sold on the market (made by Kao K.K. with a trade mark of Attack) with a washer (a dual tank washer made by Toshiba K.K. with a model No. VH-360S1) in conditions of a detergent concentration of 0.0667 mass %, amount of city water used of 30 L, a water temperature of 20° C. and a duration of washing of 10 min. Thereafter, a washing liquid was discharged, dehydration was performed for 3 min, 30 L of city water was poured, rinse was performed for 5 min and dehydration was performed for 3 min after discharge of water. Thereafter, 30 L of city water was poured again, softener compositions of Table 1 each were added at an amount of 7 ml, followed by agitation for 3 min. Thereafter, dehydration of the towels was performed, followed by natural drying.

<Softening Evaluation Method>

The bath towels treated as described above were compared with a reference cloth (a bath towel treated in a similar way with the exception that no softening composition is contained in a treatment) by 10 male panelists (in their thirties) to determine a softening performance with the following criteria and to obtain an average, wherein when an average value is in the range of 0 to 0.3, only upper limit being not included, a symbol ⊚ is given as determination, when an average value is in the range of 0.3 to 1, only upper limit being not included, a symbol ○ is given as determination, when an average value is in the range of 1 to 1.5, only upper limit being not included, a symbol Δ is given as determination and when an average value is 1.5 or higher, a symbol X is given as determination.

0 . . . very soft finish
1 . . . soft finish
2 . . . slightly soft finish
3 . . . no soft finish

TABLE 1

| Softener composition | Evaluation of softness |
|---|---|
| Softener composition A | ⊚ |
| Softener composition B | ⊚ |
| Softener composition C | ⊚ |
| Softener composition D | ⊚ |
| Softener composition E | ⊚ |
| Softener composition F | ⊚ |
| Softener composition G | ⊚ |
| Softener composition H | ○ |
| Softener composition I | ○ |
| Softener composition J | ○ |

EXAMPLE 18

A sulfated compound was obtained by sulfating a fatty alcohol mixture of stearyl alcohol and palmityl alcohol at the weight ratio of 6/4 with $SO_3$ gas. 23 g of the obtained sulfated compound was poured into a solution of 60 g of N-(3-stearoylaminopropyl)-N,N-dimethylamine and 102 g of phenoxyethanol, obtained by mixing and stirring at 50° C., while cooling in a water bath at 20° C. Having stirred for 10 minutes, a surfactant mixture in light brown was obtained.

Then, in a beaker of 1000 ml with two sets of 3 agitating blades of 3.5 cm in diameter at respective two blade positions 1.5 cm and 4 cm from the bottom of the beaker, 560 g of ion exchanged water at 60° C. was put and 185 g of the surfactant mixture obtained in the above process was added thereto over 15 sec., while agitating the ion exchanged water at 200 r/min. After the addition, the compounded material was further agitated for 3 min. Thereafter, a pH value of the compounded material was adjusted with a 6 N hydrochloric acid solution to 4.5, followed by agitation for another 2 min. Then, ion exchanged water at 60° C. was added into the compounded material so as to be 800 g in amount and thereafter, the compounded material was cooled down to 30° C. while agitating in a water bath at 20° C. to obtain a softener composition K.

Note that in the example, absolutely neither increase in viscosity nor gelation was observed during production.

EXAMPLE 19

A sulfated compound was obtained by sulfating 2-decyl-1-tetra decanol, obtained by Guerbet reaction of lauryl aldehyde.

55 g of the obtained sulfated compound was poured into a solution of 145 g of N-(3-stearoylaminopropyl)-N,N-dimethylamine and 145 g of phenoxyethanol, obtained by mixing and stirring at 50° C., while cooling in a water bath at 20° C. Having stirred for 10 minutes, a surfactant mixture in light brown was obtained.

Then, in a beaker of 1000 ml with two sets of 3 agitating blades of 3.5 cm in diameter at respective two blade positions 1.5 cm and 4 cm from the bottom of the beaker, 290 g of ion exchanged water at 60° C., 55 g of triethyleneglycol monophenylether at 60° C., 10 g of a 50% aqueous solution of citric acid at 60° and 40 g of an ethylene oxide (20 moles) adduct to lauryl alcohol melted at 60° C. were introduced and 345 g of the surfactant mixture obtained in the above process was added thereto over 15 sec., while agitating the ion exchanged water at 200 r/min. After the addition, the compounded material was further agitated for 3 min. Thereafter, a pH value of the compounded matrial was adjusted with a 6 N hydrochloric acid solution to 4.5, followed by agitation for another 2 min. Then, ion exchanged water at 60° C. was added into the compounded material so as to be 800 g in amount and thereafter, the compounded material was cooled down to 30° C. while agitating in a water bath at 20° C. to obtain a softener composition L.

EXAMPLE 20

In a continuous thin film reactor, 122.1 g of a sulfated compound obtained by sulfating $C_{24}$ Guerbet alcohol with $SO_3$ gas was poured into 100.4 g of 3-octadecanoyl amidopropyl(N,N-dimethyl)amine ($C_{18}$APA) for neutralization, while stirring and melting at 80° C., to obtain a brownish transparent liquid (in a solid state at room temperature with a melting point of 31° C.). The obtained brownish transparent liquid was a mixture of 88.5% of the compound expressed by a formula (I-1) of Example 1, 4.4% of free amines and 7.1% of the Guerbe alcohol.

EXAMPLE 21

In a continuous thin film reactor, 147.0 g of a sulfated compound obtained by sulfating $C_{24}$ Guerbet alcohol with $SO_3$ gas was poured into 100.3 g of dimethylstearyl amine (Farmin DM8098 of Kao Corporation) for neutralization, while stirring and melting at 80° C., to obtain a light yellow transparent liquid (in a solid state at room temperature with a melting point of 33° C.). The obtained yellow transparent liquid was a mixture of 87.5% of the compound expressed by the below shown formula, 5.7% of free amines and 6.7% of the Guerbet alcohol.

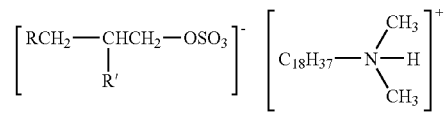

EXAMPLE 22

In a continuous thin film reactor, 127.9 g of a sulfated compound obtained by sulfating $C_{24}$ Guerbet alcohol with $SO_3$ gas was poured into 100.4 g of dimethyl-mono long chain (C16–22)alkyl amine (Farmine DM2285 of Kao Corporation) for neutralization, while stirring and melting at 80° C., to obtain a light yellow transparent liquid (in a solid state at room temperature with a melting point of 27° C.). The obtained yellow transparent liquid was a mixture of 88.1% of the compound expressed by the below shown formula, 3.2% of free amines and 8.6% of the Guerbet alcohol.

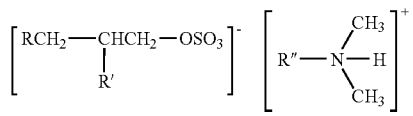
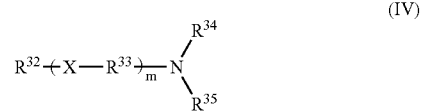

What is claimed is:

1. A sulfuric acid amine salt of formula (I):

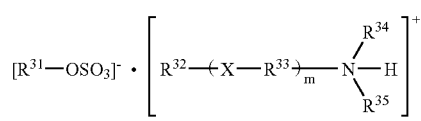

wherein in the formulae, $R^{31}$ is a branched $C_{12-26}$ alkyl or alkenyl group, or a group represented by the formula $R^{36}$-$(OA)_n$-, wherein $R^{36}$ is a linear or branched $C_{12-36}$ alkyl or alkenyl group, OA is an oxyalkylene group having 2 to 4 carbon atoms and n is a number of from 0.1 to 10 on the average;

$R^{32}$ is a linear or branched $C_{10-36}$ alkyl or alkenyl group;

X is —CONH—, —NHCO—, —COO— or —OCO—;

$R^{33}$ is a linear or branched $C_{1-6}$ alkylene group;

$R^{34}$ is a linear or branched $C_{1-6}$ alkyl or hydroxyalkyl group, or a group represented by $R^5$—[B—$R^6$]$_b$—, wherein $R^5$ is a linear or branched $C_{10-36}$ alkyl or alkenyl group, $R^6$ is a linear or branched $C_{1-6}$ alkylene group, B is a group selected from the group consisting of —COO—, —OCO—, —CONH— and —NHCO—, b is a number of 0 or 1;

$R^{35}$ is a linear or branched $C_{1-6}$ alkyl or hydroxyalkyl group; and m is a number of 0 or 1, said sulfuric acid amine salt is obtained by a process comprising:

mixing and neutralizing a compound represented by the formula (III) (hereinafter referred to as the compound (III)):

$$R^{31}—OSO_2OH \quad (III)$$

wherein $R^{31}$ indicates the same meaning as in the above description, which has been obtained by sulfating an alcohol (hereinafter referred to as an alcohol (II)) represented by the formula (II):

$$R^{31}—OH \quad (II)$$

wherein $R^{31}$ indicates the same meaning as in the above description, with a molten amine (hereinafter referred to as an amine (IV)) represented by the formula (IV):

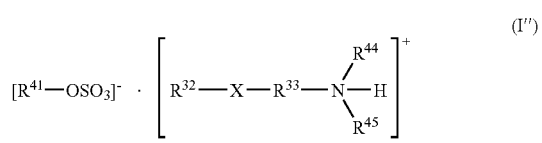

wherein in the formula (IV), $R^{32}$, X, $R^{33}$, $R^{34}$, $R^{35}$ and m indicate the respective same meanings as in the above description for formula (I).

2. A sulfuric acid amine salt (hereinafter referred to as a sulfuric amine salt (I″)) represented by the formula (I″):

wherein in the formula, $R^{41}$ is a branched $C_{18-36}$ alkyl or alkenyl group, or a group represented by the formula $R^{36}$-$(OA)_n$-, wherein $R^{36}$ is a linear or branched $C_{12-36}$ alkyl or alkenyl group, OA is an oxyalkylene group having 2 to 4 carbon atoms and n is a number of from 0.1 to 10 on average; $R^{32}$ is a linear or branched $C_{10-36}$ alkyl or alkenyl group; X is —CONH—, —NHCO—, —COO— or —OCO—; $R^{33}$ is a linear or branched $C_{1-6}$ alkylene group; each of $R^{44}$ and $R^{45}$ is, independently of the other, a hydrogen atom, a linear or branched $C_{1-6}$ alkyl, alkenyl or hydroxyalkyl group, or a group represented by the formula $R^{32}$—X—$R^{33}$—, wherein $R^{32}$, X and $R^{33}$ indicate the respective above meanings.

3. A composition comprising the sulfuric acid amine salt (I) according to claim 1 or the sulfuric acid amine salt (I″) according to claim 2 and a solvent.

4. A softening composition comprising:

at least one ingredient selected from the group consisting of an inorganic salt, an ester compound of saturated or unsaturated fatty acid having 8 to 22 carbon atoms, a polyvalent alcohol, a sequestering agent, an antioxidant, an organic acid, a perfume and a colorant; and the sulfuric acid amine salt (I) according to claim 1 or the sulfuric acid amine salt (I″) according to claim 2 as a softener.

5. A softening composition comprising:

at least one ingredient selected from the group consisting of an inorganic salt, an ester compound of saturated or unsaturated fatty acid having 8 to 22 carbon atoms, a polyvalent alcohol, a sequestering agent, an antioxidant, an organic acid, a perfume and a colorant; and the obtained sulfuric acid amine salt (I) represented by the formula (I) of claim 1 as a softener.

6. The sulfuric acid amino salt (I) of claim 1, wherein $R^{31}$ is a $C_{18-28}$ Guerbet alkyl group.

7. The sulfuric acid amino salt (I) of claim 1, wherein m is 1 in formula (I).

* * * * *